United States Patent [19]

Mayer et al.

[11] 4,369,206
[45] Jan. 18, 1983

[54] AMMONIUM SALTS OF α-KETOCARBOXYLIC ACIDS

[75] Inventors: Wofram Mayer; Hans Rudolph, both of Krefeld; Eckhard de Cleur, Duisburg; Manfred Schönfelder, Leverkusen, all of Fed. Rep. of Germany

[73] Assignee: Bayer Aktiengesellschaft, Leverkusen, Fed. Rep. of Germany

[21] Appl. No.: 54,315

[22] Filed: Jul. 2, 1979

[30] Foreign Application Priority Data

Jul. 14, 1978 [DE] Fed. Rep. of Germany ....... 2830953

[51] Int. Cl.³ .............................................. B05D 3/06
[52] U.S. Cl. ............................. 427/54.1; 204/159.22; 204/159.23; 204/159.24; 260/501.1; 260/501.17; 260/501.18; 260/501.2; 427/386; 427/388.2; 427/389; 427/389.7; 427/389.9; 427/391; 427/393.5; 427/393.6; 525/454; 525/526; 525/529; 528/44; 528/49; 528/75; 528/114; 528/205; 544/107; 544/402; 546/168; 546/314; 546/315; 548/325; 548/335; 549/70
[58] Field of Search ........... 260/501.1, 501.17, 501.18, 260/501.2, 32.8 EP, 33.2 EP, 33.6 EP, 31.4 EP, 465, 501.15, 501.16, 346.22, 347.3, 465.4, 32.8 EP, 33.2 EP, 33.6 EP, 31.4 EP; 562/433, 442, 443, 459, 460, 461, 462, 577, 575, 567, 435, 493, 598, 574; 560/51, 52, 53, 176, 183, 125, 126, 128, 170; 526/317; 525/454, 526, 529; 528/44, 49, 75, 113, 114, 205; 427/54.1, 386, 385.5, 388.1, 388.2, 421, 393.6, 389, 389.9, 391, 393.5, 389.7, 384, 430.1, 435, 428; 204/159.14, 159.15, 159.19, 159.22, 159.23, 159.24; 546/168, 314, 315; 544/402, 107; 548/335, 325; 549/70

[56] References Cited

U.S. PATENT DOCUMENTS

3,338,804 8/1967 Fischer .............................. 204/48
3,862,150 1/1975 Bechara et al. ................ 562/459 X
4,191,840 3/1980 Sellstedt et al. ................ 562/434 X

FOREIGN PATENT DOCUMENTS

1642 12/1961 France .
1455695 11/1976 United Kingdom .

OTHER PUBLICATIONS

Chemical Abstracts Band 48, Nr. 15 8/10/54.
P. Simonart et al., "The Amino-Acid Metabolism in Aspergillus Oryzae, III. Free Amino Acids in the Mycelium Grown on Different carbon Sources in Presence of Ammonia", Spalten 8872 I bis 8873 A & Antonie van Leeuwenhoek, J. Microbiol., Serol Band 20, 1954 Seiten 174 bis 180.
Handbook for Organic Chemistry, Beilstein, 4th Edition, 2nd Supplement, vol. 10, p. 454.
Chemisches Zentralblatt, Mar.-Apr., 1937 pp. 2145-2146.
Houben-Weyl, Method der Organischen Chemie, vol. XI No. 1, pp. 961-963.
The Condensed Chemical Dictionary, Eighth Edition, van Nostrand Reinhold Co. N.Y. (1971), p. 55.
Morrison et al., Organic Chemistry Allyn & Bacon Inc. Boston (1963), pp. 675-679.
Concise Chemical and Technical Dictionary, Chemical Publishing Co. N.Y. (1962), p. 49.
J. C. Craig et al., J. Org. Chem., 31 871 (1968).

*Primary Examiner*—Thurman K. Page
*Attorney, Agent, or Firm*—Gene Harsh; Lawrence S. Pope; Thomas W. Roy

[57] ABSTRACT

This invention relates to new ammonium salts of α-ketocarboxylic acids, to their use for the production of amines in situ by photochemical decomposition and to photochemically hardenable coating compositions containing these ammonium salts.

7 Claims, No Drawings

AMMONIUM SALTS OF α-KETOCARBOXYLIC ACIDS

BACKGROUND OF THE INVENTION

By virtue of their very wide range of chemical and physical properties, monoamines and polyamines are used as reactants in a variety of different chemical reactions. Reference is merely made here to their catalytic activity in numerous chemical reactions attributable to their basicity and to their use as crosslinking agents for polyurethane and epoxide resins. For many applications, it is desirable not to use the free amines, but instead to add the amines to the reaction mixture in a masked form from which they are released at a specific time to initiate the required reaction.

It is possible, for example, to release amines from enamines, ketimines and aldimines by the addition of water. Unfortunately, one disadvantage of these compounds lies in their high sensitivity to moisture; tertiary amine nitrogen atoms cannot be blocked in this way. It is also known that amines can be released from quaternary ammonium salts by heating to above 100° C. (Houben-Weyl, Methoden der Organischen Chemie, Vol. XI, 1). In many cases, however, it is desired to release the amines at considerably lower temperatures.

It has now surprisingly been found that amines can be released from ammonium salts of α-ketocarboxylic acids, even at room temperature, under the action of light having a wavelength in the range of from about 250 to 500 nm, the ketocarboxylic acid undergoing decarboxylation.

SUMMARY OF THE INVENTION

Accordingly, the present invention relates to ammonium salts of α-ketocarboxylic acids corresponding to the following general formula:

$$A-CO-COOH \tag{I}$$

wherein

A represents hydrogen, a hydroxyl or carboxyl group, —COR, —NO$_2$, —CN, an optionally branched alkyl radical containing from about 1 to 6 carbon atoms, preferably about 1 to 2 carbon atoms, which may optionally be substituted by halogen, —OH, —COOH, —COOR, —CN, —OR, —COR or —COR', a cycloalkyl radical containing from about 4 to 10, preferably 6, carbon atoms, an aryl or aralkyl radical containing from about 6 to 15, preferably from about 6 to 10 carbon atoms which may optionally be substituted by —OH, —R, —OR, —SR, halogen, —NO$_2$, —COR, —COOH, —CN, —COOR, —CONH$_2$, —OR', —SR' or —COR', or a C$_4$–C$_{10}$, preferably C$_5$–C$_9$- heterocyclic radical containing oxygen and/or nitrogen as a hetero atom, wherein R represents an optionally halogen substituted alkyl group containing from about 1 to 6 carbon atoms preferably methyl, ethyl, isopropyl or tert.butyl and R' represents an aryl group containing from about 6 to 12 carbon atoms, preferably phenyl.

The present invention also relates to a process for releasing an amine from its blocked form, characterized in that the salt of the amine with an α-ketocarboxylic acid corresponding to general formula I above is irradiated with light having a wavelength in the range of from about 250 to 500 nm and/or is heated to around 50°–130° C. and preferably to about 50°–80° C.

The present invention also relates to coating compositions based on polyurethane or epoxide resin precursors hardening in the presence of amines, characterized in that they contain from about 0.1 to 40% by weight, preferably from about 0.3 to 15% by weight, based on solids, of the ammonium salts described above and, optionally, sensitizers.

DETAILED DESCRIPTION OF THE INVENTION

Examples of acids corresponding to general formula I suitable for use in accordance with the present invention are glyoxylic acid, pyruvic acid, cyclobutyl glyoxylic acid, cyclopentyl glyoxylic acid, cyclohexyl glyoxylic acid, cyclohexenyl glyoxylic acid, trichloropyruvic acid, methoxy pyruvic acid, acetyl pyruvic acid, oxalic acid, mesoxalic acid, oxaloacetic acid, methyl oxaloacetic acid, phenyl pyruvic acid, benzyl pyruvic acid, benzoyl pyruvic acid, p-chlorophenyl pyruvic acid, naphthoyl pyruvic acid, diethoxy pyruvic acid, furyl pyruvic acid, pyridine pyruvic acid, mercapto pyruvic acid, phenyl glyoxylic acid, p-chlorophenyl glyoxylic acid, p-methoxy phenyl glyoxylic acid, p-nitrophenyl glyoxylic acid, naphthyl glyoxylic acid, anthracene glyoxylic acid, azulene glyoxylic acid, benzimidazole glyoxylic acid, benzofuran glyoxylic acid, benzoxazine glyoxylic acid, furyl glyoxylic acid, pyridine glyoxylic acid, quinoline glyoxylic acid and thiophene glyoxylic acid.

According to the present invention, it is preferred to use oxalic acid, pyruvic acid, phenyl pyruvic acid and, in particular, phenyl glyoxylic acid, phenyl glyoxylic acid substituted on the aromatic ring by C$_1$–C$_3$-alkyl, C$_1$–C$_3$-alkoxy, hydroxy or nitro groups, halogen or a phenyl radical, and also α-naphthyl glyoxylic acid.

Suitable amine components for the ammonium salts according to the present invention are any compounds containing one or more primary and/or secondary and-/or tertiary (preferably tertiary) amine nitrogen atoms and having a molecular weight of from about 31 to 500, preferably from about 100 to 300. These compounds preferably contain from about 1 to 5 amine nitrogen atoms and, with particular preference, from about 1 to 3 amine nitrogen atoms and, in addition, may contain other functional groups, such as hydroxyl, mercapto, ether, thioether, amide and ester groups or even halogen atoms.

Examples of amines suitable for use in accordance with the present invention are methylamine, dimethylamine, ethylamine, diethylamine, ethanolamine, diethanolamine, tertiary amines, such as triethylamine, tributylamine, N-methylmorpholine, N-ethyl morpholine, N,N,N',N'-tetramethyl ethylene diamine, pentamethyl diethylene triamine and higher homologs (German Offenlegungsschrift Nos. 2,624,527 and 2,624,528), 1,4-diazabicyclo-[2,2,2]-octane, N-methyl-N'-dimethylaminoethyl piperazine, bis-(dimethylaminoalkyl)-piperazines (German Offenlegungsschrift No. 2,636,787), N,N-dimethyl benzylamine, N,N-dimethyl cyclohexylamine, N,N-diethyl benzylamine, bis-(N,N-diethylaminoethyl)-adipate, N,N,N',N'-tetramethyl-1,3-butane diamine, N,N-dimethyl-β-phenylethylamine, 1,2-dimethyl imidazole, 2-methyl imidazole, monocyclic and bicyclic amidines (German Offenlegungsschrift No. 1,720,633), bis-(dialkylamino)-alkyl ethers (U.S. Pat. No. 3,330,782, German Auslegesschrift No.

1,030,558, German Offenlegungsschrift Nos. 1,804,361 and 2,618,280) and tertiary amines containing amide groups (preferably formamide groups) according to German Offenlegungsschrift Nos. 2,523,633 and 2,732,929); tertiary amines containing active hydrogen atoms, for example triethanolamine, triisopropanolamine, N-methyl diethanolamine, N-ethyl diethanolamine, N,N-dimethyl ethanolamine, their reaction products with alkylene oxides, such as propylene oxide and-/or ethylene oxide, also secondary-tertiary amines according to German Offenlegungsschrift No. 2,732,292; silaamines containing carbon-silicon bonds of the type described, for example, in German Patent 1,229,290 (corresponding to U.S. Pat. No. 3,620,984), for example 2,2,4-trimethyl-2-silamorpholine and 1,3-diethylaminomethyl tetramethyl disiloxane.

Primary aliphatic diamines suitable for use in accordance with the present invention are, for example, ethylene diamine, 1,4-tetramethylene diamine, 1,11-undecamethylene diamine, 1,12-dodecamethylene diamine and mixtures thereof, 1-amino-3,3,5-trimethyl-5-aminomethyl cyclohexane ("isophorone diamine"), 2,4- and 2,6-hexahydrotolylene diamine and mixtures thereof, perhydro-2,4'- and 4,4'-diaminodiphenyl methane, p-xylylene diamine, bis-(3-aminopropyl)-methylamine, diaminoperhydro anthracenes (German Offenlegungsschrift No. 2,638,731 and cycloaliphatic triamines according to German Offenlegungsschrift No. 2,614,244. It is also possible in accordance with the present invention to use hydrazine and substituted hydrazines, for example, methyl hydrazine, N,N'-dimethyl hydrazine and their homologs, also acid dihydrazides, for example, carbodihydrazide, oxalic acid dihydrazide, and dihydrazides of malonic acid, succinic acid, glutaric acid, adipic acid, β-methyl adipic acid, sebacic acid, hydraacrylic acid and terephthalic acid; semicarbazido alkylene hydrazides such as β-semicarbazido propionic acid hydrazide (German Offenlegungsschrift No. 1,770,591), semicarbazido alkylene carbazinic esters such as 2-semicarbazidoethyl carbazinic ester (German Offenlegungsschrift No. 1,918,504) or even amino semicarbazide compounds such as β-aminoethyl semicarbazido carbonate (German Offenlegungsschrift No. 1,902,931).

Examples of primary aromatic diamines are bisanthranilic acid esters according to German Offenlegungsschrift Nos. 2,040,644 and 2,160,590, 3,5- and 2,4-diaminobenzoic acid esters according to German Offenlegungsschrift No. 2,025,900, the diamines containing ester groups described in German Offenlegungsschrift Nos. 1,803,635 (U.S. Pat. Nos. 3,681,290 and 3,736,350), 2,040,650 and 2,160,589, the diamines containing ether groups according to German Offenlegungsschrift Nos. 1,770,525 and 1,809,172 (U.S. Pat. Nos. 3,654,364 and 3,736,295), 2-halogen-1,3-phenylene diamines optionally substituted in the 5-position (German Offenlegungsschrift Nos. 2,001,772, 2,025,896 and 2,065,869), 3,3'-dichloro-4,4'-diaminodiphenyl methane, tolylene diamine, 4,4'-diaminodiphenyl methane, 4,4'-diaminodiphenyl disulfides (German Offenlegungsschrift No. 2,404,976), diaminodiphenyl dithioethers (German Offenlegungsschrift No. 2,509,404), aromatic diamines substituted by alkyl thio groups (German Offenlegungsschrift No. 2,638,760), diaminobenzene phosphonic acid esters (German Offenlegungsschrift No. 2,459,491), aromatic diamines containing sulphonate or carboxylate groups (German Offenlegungsschrift No. 2,720,166) and the high-melting diamines according to German Offenlegungsschrift No. 2,635,400. Examples of aliphatic-aromatic diamines are the aminoalkyl thioanilines according to German Offenlegungsschrift No. 2,734,574.

Monoamines suitable for use in accordance with the present invention are butyl and dibutylamine, octylamine, stearylamine, N-methyl stearylamine, pyrrolidine, piperidine and cyclohexamine.

Amines preferably used in accordance with the present invention are tert.-butylamine, diethylamine, diethanolamine, triethylamine, di- and tri-butylamine, N,N-dimethyl benzylamine, diazabicyclooctane (DABCO), and diazabicycloundecene (DBU).

It is known from the literature that certain α-ketocarboxylic acids are decomposed on heating in the presence of amines (J. C. Craig and L. R. Kray in J. Org. Chem. 31, 871 (1968); S. D. Paul and G. D. Pradham, Indian J. Chem. 9, 318 (1971)). Benzaldehyde-d₁, for example is obtained from phenyl glyoxylic acid-d₁ on heating to 130° C. in the presence of N-ethyl morpholine. The free ammonium salts are, however, novel.

The ammonium salts according to the present invention are generally crystalline compounds having a defined melting point. They are soluble in numerous organic solvents, for example, acetone, acetonitrile, chloroform, methylene chloride, methanol, ethanol and ethylene glycol monomethyl ether acetate.

The ammonium salts according to the present invention may be readily obtained by reacting the α-ketocarboxylic acids corresponding to general formula I, with the amine component at temperatures in the range of from about −20° to +50° C., preferably at room temperature, optionally in the presence of an organic solvent, such as ether, benzene, toluene, chlorobenzene, petroleum ether, acetone, dioxane, chloroform, etc. In general, approximately 1 mol of the ketocarboxylic acid is used per amine equivalent. With many diamines (for example, ethylene diamine or diazabicyclooctane), it is also possible to use salts with only one equivalent of α-ketocarboxylic acid (i.e. the monoammonium salts) as latent initiators according to the present invention. Accordingly, the present invention also covers polyamines of this type which are only partly neutralized with the α-ketocarboxylic acids corresponding to formula I. It is also possible by carrying out a simple preliminary test to determine how many amine nitrogen atoms of a polyamine have to be converted into the ammonium salt form to obtain the required deactivation.

As mentioned, the parent amines may be released at any desired time from the ammonium salts according to the present invention by photochemical decomposition under very mild conditions (temperatures as low as room temperature), i.e. by irradiation with light having a wavelength of from about 250 to 500 nm, preferably from about 300 to 400 nm.

Accordingly, the present invention also relates to a process for releasing an amine from its blocked form, characterized in that the salt of the amine with an α-ketocarboxylic acid corresponding to general formula I:

$$A-CO-COOH \qquad (I)$$

wherein

A is defined as above, is irradiated with light having a wavelength in the range of from about 250 to 500 nm and/or heated to around 50°–130° C. and preferably to about 50°–80° C.

According to the present invention, it is advantageous to sensitize the photoreaction by the addition of triplet sensitizers known per se, such as benzophenone, acetophenone, propiophenone, xanthone, thioxanthone or triphenylene. These sensitizers are preferably added in a quantity of from about 0.1 to 30% by weight and, with particular reference, in a quantity of from about 3 to 10% by weight, based on ammonium salt.

The ammonium salts according to the present invention are particularly suitable for use as UV-activatable hardening catalysts for resins or resin compositions. Resins of the type in question are, for example, epoxy resins or lacquers based on isocyanates which are used either as such, in chemically modified form or in admixture with other resins.

Lacquer coatings having a crosslinked high molecular weight polyurethane structure obtained from polyhydroxyl compounds and polyisocyanates by the isocyanate-polyaddition process are already known. These commercially valuable coatings may be applied both by hand and also by machine, for example, by spray coating, dip coating or casting. In practice, they are applied either by the so-called two-component process or by the one-component process. In the two-component process, the two components (polyisocyanate on the one hand; isocyanate-reactive compound on the other hand) are mixed, optionally in the presence of a solvent. The two components can only be completely prevented from reacting by using masked polyisocyanates which only release the free isocyanate on heating. The use of systems such as these, however, is limited to stoving lacquers. Nevertheless, the lacquer mixtures containing free polyisocyanates also have a more or less long pot life which enables the lacquers to be satisfactorily applied by hand or machine to the substrates on which they subsequently harden and crosslink to form polyurethanes. In contrast, one-component systems contain an adduct with free isocyanate groups of polyhydroxyl compound and an excess of polyisocyanate, crosslinking taking place after application by reaction of the free NCO-groups in the lacquer with water (atmospheric moisture). In this case, too, it is important to ensure that the lacquer does not undergo premature crosslinking during storage by keeping atmospheric moisture away and/or by adding water-removing agents.

On the other hand, it is desirable for the lacquer to crosslink and dry as quickly as possible after it has been applied to the substrate. Both in the case of one-component lacquers and in the case of two-component lacquers, it is possible to promote the hardening reaction by the addition of reacton accelerators known per se. The need, however, for an accelerated crosslinking reaction on the substrate conflicts with the equally important need for as long a pot life as possible. In principle, it would be possible to add a catalyst to the lacquer mixture just before it is applied to the substrate. Although this may be possible in the case of small-scale manual coating processes, it is not possible in the case of large-scale machine coating processes because the lacquer mixtures have relatively long residence times in the machine, in some cases at elevated temperature, and because an undesired reduction in pot life by the accelerating effect of the catalyst is unavoidable. Even applying the catalyst after the lacquer mixture has been coated onto the substrate has been considered, for example, by spraying it on in gaseous form, although this requires additional elaborate machines. In addition, only a few catalysts can be processed in this way.

It is known from German Offenlegungsschrift No. 1,621,883 that a lacquer layer of a physically drying binder containing a catalyst known per se for isocyanate-polyaddition reactions can be initially applied to the surface to be lacquered, followed by the application of a catalyst-free polyurethane lacquer. In this way, it is possible to considerably shorten the drying time of a polyurethane lacquer mixture without affecting either its shelf life or its processibility. The additional expense, however, incurred by the second lacquer coating is a disadvantage.

Basically, the same problems which are encountered in the one-component and two-component polyurethane systems described above also arise in the case of coating compositions based on epoxy resins wherein the crosslinking again generally has to be catalyzed by tertiary amines. To this end, it is proposed in German Offenlegungsschrift No. 2,357,859 to add salts of tertiary amines with certain α-substituted carboxylic acids to the coating compositions. When heated to between about 70° and 200° C., these ammonium salts decompose through decarboxylation, after which the coating rapidly hardens under the catalytic influence of the amine liberated. One disadvantage of this procedure is that the coating has to be heated to relatively high temperatures. This is undesirable with numerous substrates.

With the ammonium salts according to the present invention it is now possible to obtain masked tertiary amine catalysts which enable the coating to be rapidly hardened by irradiation with short-wave light, even at temperatures as low as room temperature, and which give lacquer coatings having a particularly glossy surface. On the other hand, the amines may be released from the ammonium salts according to the invention by heating to about 50°–130° C.

Accordingly, the present invention also relates to coating compositions based on polyurethane or epoxide resin precursors hardening in the presence of amines, characterized in that they contain from about 0.1 to 40% by weight, preferably from about 0.3 to 15% by weight, based on solids, of the ammonium salts according to the present invention and, optionally, sensitizers.

The coating compositions according to the present invention may be based on the one-component and two-component polyurethane systems crosslinking in the presence of amines which are known per se in the lacquer and coating art. As briefly mentioned above, one-component systems are prepolymers, optionally dissolved in inert organic solvents containing from about 1 to 25% by weight, preferably from about 2.5 to 19% by weight of free NCO-groups which have been produced by reacting relatively high molecular weight and/or low molecular weight compounds containing isocyanate-reactive groups, of the type described hereinafter, with an excess of polyisocyanates of the type described hereinafter. Two-component polyurethanes are a mixture, optionally dissolved in an inert organic solvent, of a relatively high molecular weight polyhydroxyl compound (for example, a hydroxyl-containing prepolymer of polyisocyanate and an excess of polyol) on the one hand and a polyisocyanate on the other hand.

The coating compositions according to the present invention may contain aliphatic, cycloaliphatic, araliphatic, aromatic and heterocyclic polyisocyanates of the type described, for example, by W. Siefken in Justus Liebigs Annalen der Chemie, 562, pages 75 to 136, for example, those corresponding to the following general formula:

wherein:

n represents about 2–4, preferably 2, and

Q represents an aliphatic hydrocarbon radical containing from about 2 to 18 carbon atoms, preferably from about 6 to 10 carbon atoms, a cycloaliphatic hydrocarbon radical containing from about 4 to 15, preferably from about 5 to 10 carbon atoms, an aromatic hydrocarbon radical containing from about 6 to 15 carbon atoms, preferably from about 6 to 13 carbon atoms, or an araliphatic hydrocarbon radical containing from about 8 to 15 carbon atoms, preferably from about 8 to 13 carbon atoms. Examples are as follows: ethylene diisocyanate, 1,4-tetramethylene diisocyanate, 1,6-hexamethylene diisocyanate, trimethyl hexamethylene diisocyanate, 1,12-dodecane diisocyanate, cyclobutane-1,3-diisocyanate, cyclohexane-1,3- and -1,4-diisocyanate and mixtures of these isomers, 1-isocyanato-3,3,5-trimethyl-5-isocyanatomethyl cyclohexane (German Auslegeschrift No. 1,202,785, U.S. Pat. No. 3,401,190), 2,4- and 2,6-hexahydrotolylene diisocyanate and mixtures of these isomers, hexahydro-1,3- and/or -1,4-phenylene diisocyanate, perhydro-2,4'- and/or -4,4'-diphenyl methane diisocyanate, 1,3- and 1,4- phenylene diisocyanate, 2,4- and 2,6-tolylene diisocyanate and mixtures of these isomers, diphenyl methane-2,4'- and/or -4,4'-diisocyanate, and naphthylene-1,5-diisocyanate.

According to the present invention, it is also possible, for example, to use triphenyl methane-4,4',4''-triisocyanate, polyphenyl polymethylene polyisocyanates of the type obtained by condensing aniline with formaldehyde, followed by phosgenation, and described, for example, in British Pat. Nos. 874,430 and 848,671, m- and p-isocyanatophenyl sulphonyl isocyanates according to U.S. Pat. No. 3,454,606, perchlorinated aryl polyisocyanates of the type described, for example, in German Auslegeschrift No. 1,157,601 (U.S. Pat. No. 3,277,138), polyisocyanates containing carbodiimide groups of the type described in German Pat. No. 1,092,007 (U.S. Pat. No. 3,152,162) and in German Offenlegungsschrift Nos. 2,504,400, 2,537,685 and 2,552,350, norbornane diisocyanates according to U.S. Pat. No. 3,492,330, polyisocyanates containing allophanate groups of the type described, for example, in British Pat. No. 994,890, in Belgian Pat. No. 761,626 and in Dutch Patent Application No. 7,102,524, polyisocyanates containing isocyanurate groups of the type described, for example, in U.S. Pat. No. 3,001,973, in German Pat. Nos. 1,022,789, 1,222,067 and 1,027,394 and in German Offenlegungsschrift Nos. 1,929,034 and 2,004,048, polyisocyanates containing urethane groups of the type described, for example, in Belgian Pat. No. 752,261 or in U.S. Pat. Nos. 3,394,164 and 3,644,457, polyisocyanates containing acylated urea groups according to German Pat. No. 1,230,778, polyisocyanates containing biuret groups of the type described, for example, in U.S. Pat. Nos. 3,124,605, 3,201,372 and 3,124,605 and in British Pat. No. 889,050, polyisocyanates produced by telomerization reactions of the type described for example in U.S. Pat. No. 3,654,106, polyisocyanates containing ester groups of the type described, for example, in British Pat. Nos. 965,474 and 1,072,956, in U.S. Pat. No. 3,567,763 and in German Pat. No. 1,231,688, reaction products of the above-mentioned diisocyanates with acetals according to German Patent 1,072,385 and polyisocyanates containing polymeric fatty acid esters according to U.S. Pat. No. 3,455,883.

It is also possible to use the isocyanate-group-containing distillation residues obtained in the commercial production of isocyanates, optionally in solution in one or more of the above-mentioned polyisocyanates. It is also possible to use any mixtures of the above-mentioned polyisocyanates.

Preferred polyisocyanates are hexamethylene diisocyanate, its isocyanurate and its biuret; 1-isocyanato-3,3,5-trimethyl-5-isocyanatomethyl cyclohexane (isophorone diisocyanate); the tolylene diisocyanates and their isocyanurates; the mixed isocyanurate of tolylene diisocyanate and hexamethylene diisocyanate; the reaction product of 1 mol of trimethylol propane and 3 mols of tolylene diisocyanate and also crude diphenyl methane diisocyanate.

Suitable relatively high molecular weight compounds containing at least 2 isocyanate-reactive hydrogen atoms are those having a molecular weight of generally from about 400 to 50,000. In addition to compounds containing amino groups, thiol groups or carboxyl groups, compounds such as these are preferably compounds containing hydroxyl groups, particularly compounds containing from about 2 to 8 hydroxyl groups and, above all, compounds having a molecular weight of from about 500 to 25000, preferably from about 700 to 20000, for example, polyesters, polyethers, polythioethers, polyacetals, polycarbonates and polyester amides containing at least 2, generally from about 2 to 8, but preferably from about 2 to 4 hyroxyl groups, or even OH-prepolymers of these compounds and a less than equivalent quantity of polyisocyanate, of the type known per se for the production of homogeneous and cellular polyurethanes.

(a) The polyesters containing hydroxyl groups suitable for use in accordance with the present invention are, for example, reaction products of polyhydric, preferably dihydric and, optionally, trihydric alcohols with polybasic, preferably dibasic, carboxylic acids. Instead of using the free polycarboxylic acids, it is also possible to use the corresponding polycarboxylic acid anhydrides or corresponding polycarboxylic acid esters of lower alcohols or mixtures thereof for producing the polyesters. The polycarboxylic acids may be aliphatic, cycloaliphatic, aromatic and/or heterocyclic and may optionally be substituted, for example by halogen atoms, and/or unsaturated.

Examples of carboxylic acids such as these and their derivatives are succinic acid, adipic acid, suberic acid, azelaic acid, sebacic acid, phthalic acid, isophathalic acid, terephthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimerized and trimerized unsaturated fatty acids, optionally in admixture with monomeric unsaturated fatty acids, such as oleic acid, terephthalic acid dimethyl ester and terephthalic acid-bis-glycol ester. Suitable polyhydric alcohols are, for example, ethylene glycol, 1,2- and 1,3-propylene glycol, 1,4- and 2,3-butylene glycol, 1,6-hexane diol, 1,8-octane diol, neopentyl glycol, 1,4-bis-hydroxymethyl cyclohexane, 2-methyl-1,3-propane diol, glycerol, trimethylol propane, 1,2,6-hexane triol, 1,2,4-butane triol, trimethylol ethane, pentaerythritol, quinitol, mannitol, sorbitol, formitol, methyl glycoside, also diethylene glycol, triethylene glycol, tetraethylene glycol and higher polyethylene glycols, dipropylene glycol and higher polypropylene glycols, dibutyl glycol and higher polybutylene glycols. The polyesters may contain terminal carboxyl groups. Polyesters of lactones, for example, ε-caprolactone, or of hydroxy carboxylic acids, for example, ω-hydroxy caproic acid, may also be used.

(b) The polyethers containing at least 2, generally about 2 to 8 and preferably about 2 or 3 hydroxyl groups suitable for use in accordance with the invention are also known per se and are obtained, for example, by polymerizing epoxides, such as ethylene oxide, propylene oxide, butylene oxide, tetrahydrofuran, styrene oxide or epichlorhydrin on their own, for example, in the presence of Lewis catalysts, such as $BF_3$, or by the addition of the epoxides, preferably ethylene oxide and propylene oxide, optionally in admixture or successively, with starter components containing reactive hydrogen atoms, such as water, alcohols, ammonia or amines, for example, ethylene glycol, 1,3-propylene glycol or 1,2-propylene glycol, trimethylol propane, glycerol, sorbitol, 4,4'-dihydroxy diphenyl propane, aniline, ethanolamine or ethylene diamine. Sucrose polyethers of the type described, for example, in German Auslegeschrift Nos. 1,176,358 and 1,064,938 and formitol- or formose-started polyethers (German Offenlegungsschrift Nos. 2,639,083 and 2,737,951) may also be used in accordance with the present invention. In many cases, it is preferred to use polyethers which predominantly contain primary OH-groups (up to about 90% by weight, based on all the OH-groups present in the polyether). Polybutadienes containing OH-groups are also suitable for use in accordance with the present invention.

(c) Among the polythioethers, reference is made in particular to the condensation products of thiodiglycol on its own and/or with other glycols, dicarboxylic acids, formaldehyde, aminocarboxylic acids or amino alcohols. Depending on the co-components, the products in question are, for example, polythio mixed ethers, polythioether esters or polythioether ester amides.

(d) Suitable polyacetals are, for example, the compounds obtainable from glycols, such as diethylene glycol, triethylene glycol, 4,4'-dioxethoxy diphenyl dimethyl methane, hexane diol and formaldehdye. Polyacetals suitable for use in accordance with the present invention may also be obtained by polymerizing cyclic acetals such as trioxane (German Offenlegungsschrift No. 1,694,128).

(e) Suitable polycarbonates containing hydroxyl groups are known per se and can be obtained, for example, by reacting diols, such as 1,3-propane diol, 1,4-butane diol and/or 1,6-hexane-diol, diethylene glycol, triethylene glycol, tetraethylene glycol or thiodiglycol, with diaryl carbonates, for example, diphenyl carbonate, or phosgene (German Auslegeschrift Nos. 1,694,080, 1,915,908 and 2,221,751; German Offenlegungsschrift No. 2,605,024).

(f) The polyester amides and polyamides include, for example, the predominantly linear condensates obtained, for example, from polybasic saturated or unsaturated carboxylic acids or their anhydrides and polyhydric saturated or unsaturated amino alcohols, diamines, polyamines and mixtures thereof.

(g) Polyhydroxyl compounds already containing urethane or urea groups and optionally modified natural polyols, such as castor oil or carbohydrates, for example, starch, may also be used. Addition products of alkylene oxides with phenol/formaldehyde resins or even with urea/formaldehyde resins may also be used in accordance with the present invention.

(h) Before they are used in the polyisocyanate-polyaddition process, the above-mentioned polyhydroxyl compounds may be modified in various ways. Thus, according to German Offenlegungsschrift Nos. 2,210,839 (U.S. Pat. No. 3,849,515) and 2,544,195, a mixture of different polyhydroxyl compounds (for example, a polyether polyol and a polyester polyol) may be condensed by etherification in the presence of a strong acid to form a relatively high molecular weight polyol which is made up of different segments attached through ether bridges.

(i) According to the present invention, it is also possible to use polyhydroxyl compounds containing high molecular weight polyadducts and polycondensates or prepolymers in a finely dispersed or dissolved form. Polyhydroxyl compounds such as these are obtained, for example, by carrying out polyaddition reactions (for example, reactions between polyisocyanates and amino-functional compounds) and polycondensation reactions (for example, between formaldehyde and phenols and-/or amines) in situ in the above-mentioned compounds containing hydroxyl groups. Processes such as these are described, for example, in German Auslegeschrift Nos. 1,168,075 and 1,260,142 and in German Offenlegungsschrift Nos. 2,324,134, 2,423,984, 2,512,385, 2,513,815, 2,550,796, 2,550,797, 2,550,833, 2,550,862, 2,633,293 and 2,639,254. It it also possible, however, in accordance with U.S. Pat. No. 3,869,413 or German Offenlegungsschrift No. 2,550,860, to mix an aqueous polymer dispersion with a polyhydroxyl compound and subsequently to remove the water from the mixture.

Polyhydroxyl compounds modified by vinyl polymers of the type obtained, for example, by polymerizing styrene and acrylonitrile in the presence of polyethers (U.S. Pat. Nos. 3,383,351, 3,304,273, 3,523,093 and 3,110,695; German Auslegeschrift No. 1,152,536) or polycarbonate polyols (German Pat. No. 1,769,795; U.S. Pat. No. 3,637,909) are also suitable for use in the process according to the present invention. Plastics having particularly good flameproof properties are obtained by using polyether polyols modified in accordance with German Offenlegungsschrift Nos. 2,442,101, 2,644,922 and 2,646,141 by graft polymerization with vinyl phosphonic acid esters and, optionally (meth) acrylonitrile, (meth) acrylamide or OH-functional (meth) acrylic acid esters. Polyhydroxyl compounds into which carboxyl groups have been introduced by radical graft polymerization with unsaturated carboxylic acids and, optionally, other olefinically unsaturated monomers (German Offenlegungsschrift Nos. 2,714,291, 2,739,620 and 2,654,746) may be used particularly advantageously in combination with mineral fillers.

Where modified polyhydroxyl compounds of the type mentioned above are used as starting components in the polyisocyanate-polyaddition process, polyurethanes having considerably improved mechanical properties are formed in many cases.

Representative of the above-mentioned compounds used in accordance with the present invention are described, for example, in High Polymers, Vol. XVI, "Polyurethanes, Chemistry and Technology", by Saunders-Frisch, Interscience Publishers, New York/London, Vol., I, 1962, pages 32 to 42 and pages 44 to 54 and Vol. II, 1964, pages 5–6 and 198–199, and in Kunststoff-Handbuch, Vol. VII, Vieweg-Hochtlen, Carl-Hanser-Verlag, Munich, 1966, for example, on pages 45 to 71. It is, of course, possible to use mixtures of the above-mentioned compounds containing at least two isocyanate-reactive hydrogen atoms and having a molecular weight of from about 400 to 50,000 for example, mixtures of polyethers and polyesters.

In some cases, it is particularly advantageous to combine low-melting and high-melting polyhydroxyl compounds with one another (German Offenlegungsschrift No. 2,706,297).

Low molecular weight compounds containing at least two isocyanate-reactive hydrogen atoms (molecular weight from about 32 to 400) suitable for use in accordance with the present invention are, once again compounds preferably containing hydroxyl groups and generally containing from about 2 to 8, preferably from about 2 to 4 isocyanate-reactive hydrogen atoms.

In this case, too, it is possible to use mixtures of different compounds containing at least two isocyanate-reactive hydrogen atoms and having a molecular weight in the range of from about 32 to 400.

Examples of compounds such as these are ethylene glycol, 1,2- and 1,3-propylene glycol, 1,4- and 2,3-butylene glycol, 1,5-pentane diol, 1,6-hexane diol, 1,8-octane diol, neopentyl glycol, 1,4-bis-hydroxymethyl cyclohexane, 2-methyl-1,3-propane diol, dibromobutene diol (U.S. Pat. No. 3,723,392), glycerol, trimethylol propane, 1,2,6-hexane triol, trimethylol ethane, pentaerythritol, quinitol, mannitol, sorbitol, castor oil, diethylene glycol, triethylene glycol, tetraethylene glycol, higher polyethylene glycols having a molecular weight of up to about 400, dipropylene glycol, higher polypropylene glycols having a molecular weight of up to about 400, dibutylene glycol, higher polybutylene glycols having a molecular weight of up to about 400, 4,4′-dihydroxy diphenyl propane and dihydroxy methyl hydroquinone.

Other molecular weight polyols suitable for the purposes of the present invention are the mixtures of hydroxy aldehydes and hydroxy ketones ("formose") or the polyhydric alcohols obtained therefrom by reduction ("formitol") which are formed in the autocondensation of formaldehyde hydrate in the presence of metal compounds as catalysts and compounds capable of enediol formation as co-catalysts (German Offenlegungsschrift Nos. 2,639,084, 2,714,084, 2,714,104, 2,721,186, 2,738,154 and 2,738,512). Solutions of polyisocyanate polyaddition products, particularly solutions of polyurethane ureas containing ionic groups and/or solutions of polyhydrazodicarbonamides, in low molecular weight polyhydric alcohols may also be used as the polyol component in accordance with the present invention (German Offenlegungsschrift No. 2,638,759).

Coating systems based on epoxy resin precursors suitable for use in accordance with the present invention are, for example, triglycidyl isocyanurate; polyepoxides having a molecular weight of up to 2000, of the type obtained from bisphenol A and epichlorhydrin; bis-glycidyl esters of terephthalic acid, isophthalic acid, phthalic acid, tetrahydrophthalic acid, hexahydrophthalic acid or hexahydroterephthalic acid; triglycidyl esters of trimellitic acid; tetraglycidyl esters and β-methyl glycidyl esters of pyromellitic acid; glycidyl derivatives of hydantoin corresponding to the following general formula:

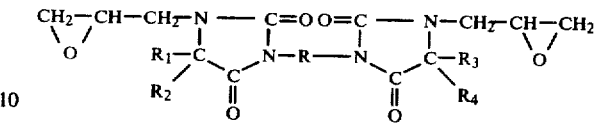

wherein $R_0$ represents a difunctional aliphatic, cycloaliphatic or araliphatic radical and $R_1$, $R_2$, $R_3$ and $R_4$ each represent a hydrogen atom or an aliphatic or cycloaliphatic hydrocarbon radical, or $R_1$ and $R_2$ or $R_3$ and $R_4$ together represent a difunctional aliphatic or cycloaliphatic hydrocarbon radical, preferably a tetramethylene or pentamethylene radical.

In the above general formula $R_1$, $R_2$, $R_3$ and $R_4$ preferably represent hydrogen or a lower alkyl radical containing from 1 to 4 carbon atoms while R preferably represents an alkylene radical containing from 1 to 4 carbon atoms.

Other polyepoxide resins suitable for the purposes of the present invention may be obtained by condensing epichlorhydrin with primary and/or secondary amines, polyesters containing hydroxyl and/or carboxyl groups, phenol/formaldehyde condensates containing hydroxyl groups or even polyether polyols. These polyepoxide resins are hardened by a known method with amines or polyamines, amides or polyamides or with polycarboxylic acids (including, for example, polyesters containing free carboxyl groups) or even with compounds containing mercapto groups or phenolic hydroxyl groups.

Other resins, such as ketone resins, nitrocellulose, PVC copolymers, cellulose acetobutyrates etc., may, of course, also be added to the lacquer systems according to the present invention in order to obtain particular properties. Other auxiliaries of the type commonly used in the lacquer art, such as levelling aids, pigments, fillers and other additives known per se, may also be used.

The coating compositions according to the present invention may contain up to about 90% by weight and preferably up to about 60% by weight of an organic solvent. Examples of suitable organic solvents are toluene, xylene, non-aromatic and substantially non-aromatic hydrocarbon fractions, ethylacetate, butylacetate, ethylene glycol monomethyl ether acetate, ethylene glycol monoethyl ether acetate, acetone, methylethyl ketone, cyclohexanone and mixtures of these compounds.

The coating compositions according to the present invention are suitable for lacquering and coating all kinds of substrates, for example, metals, such as aluminum or steel, asbestos cement, leather, textiles, rubber, paper, glass, stone and a variety of different plastics. They are particularly suitable for lacquering wood and metal.

The lacquer and coating systems according to the present invention are preferably processed by machine. They are applied by techniques known per se such as extrusion coating, spray coating, dip coating, roll coating and casting. The layer thicknesses are generally between about 1 and 1000μ, preferably between about 4 and 200μ.

After the lacquer or coating has been applied, it is irradiated with light having a wavelength of from about 250 to 500 nm. The irradiation time is generally between about 0.1 and 300 seconds, preferably between about 1 and 80 seconds, depending on the thickness of the layer applied and the power of the light source. As already explained, the ammonium salt according to the present invention which is present in the lacquer decomposes through decarboxylation under the influence of short-wave light. The amine released then acts as a catalyst for the hardening reaction or, in the case of the ammonium salt of a primary or secondary polyamide, in a known manner as a crosslinking agent, for example, for a prepolymer containing free NCO-groups.

According to the present invention, coating is preferably carried out at about room temperature (from approximately 10° to 30° C.). Since the ammonium salts according to the present invention also undergo thermal decomposition on heating, the hardening reaction may be further accelerated by heating (up to about 130° C., preferably up to about 80° C.). The advantage of the resin compositions according to the present invention, however, lies in the fact that they may also be processed at low temperatures, i.e., without any thermal stressing of the substrate.

The coating compositions according to the present invention have a surprisingly long shelf life, i.e., a long pot life, at room temperature. When irradiated with short-wave light, however, they gel extremely quickly and then harden quickly, surprisingly even when the coating systems in question are pigmented systems and not clear lacquers.

One particular advantage of the initiators according to the present invention is that they do not cause any discoloration of the lacquer on irradiation or on heating.

The invention is illustrated by the following Examples in which the quantities quoted represent parts by weight or percentages by weight, unless otherwise indicated.

EXAMPLE 1

A solution of 11 g of diazabicyclooctane (DABCO ®), in 200 ml of ether is added dropwise to a solution of 8.8 g of pyruvic acid in 50 ml of ether. The monoammonium salt of diazabicyclooctane is obtained in crystalline form in a yield of 13.5 g (67% of the theoretical yield).

EXAMPLE 2

A solution of 7.3 g of diethylamine in 50 ml of ether is added dropwise to a solution of 13 g of 3,3-dimethyl-2-oxobutyric acid in 100 ml of ether. The diethylammonium salt is obtained in crystalline form in a yield of 16.7 g (82% of the theoretical yield). M.p.: 164° C. (decomp.).

EXAMPLE 3

A solution of 14.9 g of triethanolamine in 100 ml of ether is added dropwise to a solution of 15 g of phenyl glyoxylic acid in 100 ml of ether. The triethanol ammonium salt is obtained in crystalline form in a yield of 28.1 g (94% of the theoretical yield).

EXAMPLES 4 to 9

(a) Production of substituted phenyl glyoxylic acids:
Literature:

K. Kindler et al. Chem. Ber. 76, 308 (1943)

40 g of AlCl$_3$ are dissolved at room temperature in 100–150 ml of nitrobenzene, 0.2 mol of ethoxalyl chloride is added with cooling and 0.2 mol of the substituted aromatic compound is added dropwise at 10° C. After stirring for 5 hours at room temperature, the liquid is poured onto 500 g of ice and 100 ml of HCl, extracted with ether and the organic phase is dried. After the solvent has been removed in a rotary evaporator, the residue is distilled.

The distillate consisting of the substituted phenyl glyoxylic acid ethyl ester is poured into warm 10% NaOH, stirred for 30 minutes at 40° C., acidified, extracted with ether and the ether phase is dried. After the solvent has been removed, the residue is recrystallized.

The esters and acids corresponding to the following general formula:

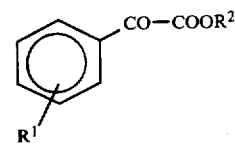

produced by the method just described have the properties set out in the following Table (φ stands for a phenyl radical):

| R$^1$ | R$^2$ | b.p. (Torr) | Melting Point (°C.) |
|---|---|---|---|
| 4-CH$_3$ | C$_2$H$_5$ | 90 (0.1) | — |
| 4-CH$_3$ | H | — | 92–95 |
| 4-CH$_2$—CH$_3$ | C$_2$H$_5$ | 110 (0.4) | — |
| 4-CH$_2$—CH$_3$ | H | — | 65–68 |
| 4-OCH$_3$ | C$_2$H$_5$ | 130 (0.4) | — |
| 4-OCH$_3$ | H | — | 91–92 |
| 4-φ | C$_2$H$_5$ | 185 (0.4) | — |
| 4-φ | H | — | 106–108 |
| 3,4-OCH$_3$ | C$_2$H$_5$ | 148 (0.3) | — |
| 3,4-OCH$_3$ | H | — | 136–137 |

The ethyl ester of α-naphthyl glyoxylic acid and the free acid were also similarly produced.

| | | b.p. (Torr) | melting point (°C.) |
|---|---|---|---|
| CO—COOR$^3$ | R$^3$ = C$_2$H$_5$ | 152 (0.5) | — |
| | H | — | 111 |

(b) Production of the ammonium salts according to the present invention:

A solution of 0.1 mol of dimethyl benzylamine in diethyl ether is added dropwise to a solution of 0.1 mol of the substituted phenyl glyoxylic acid in diethyl ether. The ammonium salts corresponding to the following general formulae:

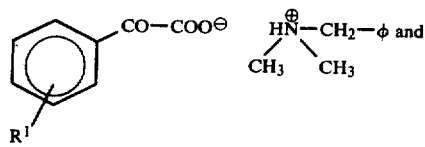

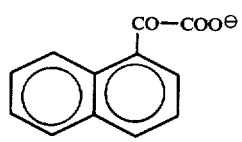

are obtained in crystalline form.

| Example No. | R$^1$ | Melting point |
| --- | --- | --- |
| 4 | 4-CH$_3$ | 115–120 |
| 5 | 4-CH$_2$—CH$_3$ | 55–64 |
| 6 | 4-OCH$_3$ | 73–81 |
| 7 | 4-φ | 106–110 |
| 8 | 3,4-OCH$_3$ | 58–62 |
| 9 | ammonium salt of α-naphthyl glyoxylic acid | 114–121 |

EXAMPLE 10

UV-hardening polyurethane lacquer

A clear lacquer consisting of:

154 parts of a polyester of 1 mol of phthalic acid anhydride, 2 mols of hexahydrophthalic acid anhydride, 3.45 mols of trimethylol propane and 1 mol of maleic acid anhydride, in the form of a 67% solution in ethylene glycol monoethyl ether acetate:xylene (1:1), 99 parts of solvent S, 3.8 parts of a 10% solution of cellulose acetobutyrate in solvent S, 120 parts of a 75% solution of an aliphatic polyisocyanate containing biuret groups (reaction product of 3 mols of hexamethylene diisocyanate and 1 mol of water) in ethylene glycol monoethyl ether acetate:xylene (1:1), which contained different quantities of initiators A and B, was applied to a glass plate in a layer thickness of 15μ.

In a second test series, a pigmented lacquer which had the same composition as the clear lacquer, but contained 222 parts of solvent S and, in addition, 114 parts of titanium dioxide white pigment, was also applied to a glass plate in a layer thickness of 15μ.

The lacquer films were irradiated for 60 seconds at a distance of 4 cm from a UV-lamp of the HT Q-4-type manufactured by Philips (power: 1 KW; maximum intensity at from about 300 to 320 nm). Thereafter, the initiator-containing lacquers (both the clear lacquer and also the pigmented lacquer) were dry to touch. In contrast, the initiator-free lacquers were still tacky.

The hardness of the lacquer films according to Konig (DIN 53 157) was then determined after storage for 1 day at room temperature after irradiation.

The results are set out in the following Table. The quantity in which the initiator is used is indicated in the Table and is based on the solids content of the lacquer.

| | No initiator | Initiator A | | | Initiator B | | |
| --- | --- | --- | --- | --- | --- | --- | --- |
| | | 3% | 4% | 5% | 3% | 4% | 5% |
| Clear lacquer | cannot be measured | 182 | 192 | 197 | 195 | 185 | 132 |
| pigmented lacquer | 150 | 185 | 185 | 188 | 193 | 192 | 200 |

Solvent S is a mixture of equal parts of methylethyl ketone, toluene, butylacetate and ethylene glycol monoethyl ether acetate; initiator A is the dimethyl benzyl ammonium salt of phenyl glyoxylic acid; initiator B is the tri-n-butyl ammonium salt of phenyl glyoxylic acid.

EXAMPLE 11

Lacquers consisting of:

264 parts of a pigmented polyol, 100 parts of the same polyisocyanate solution as in Example 10 and 7 parts of initiator were coated onto glass plates in a layer thickness of 15μ and, as described in Example 10, were irradiated, stored for 1 day and tested for hardness. The results are set out in the following Table:

| Initiator Dimethyl benzyl ammonium salt of | Pendulum hardness (seconds) |
| --- | --- |
| Phenyl glyoxylic acid | 177 |
| p-methylphenyl glyoxylic acid | 171 |
| p-ethylphenyl glyoxylic acid | 115 |
| p-methoxyphenyl glyoxylic acid | 112 |
| 3,4-dimethoxyphenyl glyoxylic acid | 98 |
| p-phenylphenyl glyoxylic acid | 149 |
| α-naphthyl glyoxylic acid | 171 |
| no initiator | cannot be measured |

The pigmented polyol consists of:

100 parts of a titanium dioxide (rutile) pigment and 164 parts of a polyester (8% of OH-groups; acid number 4) of 3 mols of phthalic acid anhydride, 0.05 mol of maleic acid anhydride and 3.5 mols of trimethylol propane, in the form of a 61% solution in ethylene glycol monoethyl ether acetate.

EXAMPLE 12

A lacquer consisting of:

264 parts of the pigmented polyol used in Example 11, 100 parts of the isocyanate solution used in Example 10 and 0.5 part of the ammonium salt of 1 mol of diazabicycloundecene and 1 mol of phenyl glyoxylic acid is applied to glass plates in a layer thickness of 60μ and stoved for 15 minutes at 80° C. After this time, the film is dry whereas a catalyst-free film is still tacky.

It is to be understood that any of the components and conditions mentioned as suitable herein can be substituted for its counterpart in the foregoing examples and that although the invention has been described in considerable detail in the foregoing, such detail is solely for the purpose of illustration. Variation can be made in the invention by those skilled in the art without departing from the spirit and scope of the invention except as is set forth in the claims.

What is claimed is:

1. A process for releasing an amine from its blocked form, characterized in that an ammonium salt of an α-ketocarboxylic acid corresponding to the following general formula:

A—CO—COOH wherein
- A represents hydrogen, a hydroxyl or carboxyl group, —COR, —CN, an optionally branched alkyl radical containing from 1 to 6 carbon atoms which may optionally be substituted by halogen, —OH, —COOH, —COOR, —CN, —OR, —COR, or COR', a cycloalkyl radical containing from about 4 to 10 carbon atoms, an aryl or aralkyl radical containing from about 6 to 15 carbon atoms which may optionally be substituted by —OH, —R, —OR, —SR, halogen, —NO$_2$, —COR, —COOH, —CN, —COOR, —CONH$_2$, —OR', —SR' or —COR', or a C$_4$-C$_{10}$—heterocyclic radical containing oxygen and/or nitrogen as a hetero atom, wherein
- R represents an optionally halogen-substituted alkyl group containing from about 1 to 6 carbon atoms and
- R' represents an aryl group containing from about 6 to 12 carbon atoms, is irradiated with light having a wavelength of from about 250 to 500 nm.

2. Coating compositions based on polyurethane or epoxy resin precursors hardening in the presence of amines, characterized in that they contain from about 0.1 to 40% by weight, based on solids content, of an ammonium salt of an α-ketocarboxylic acid corresponding to the following general formula:

A—CO—COOH wherein
- A represents hydrogen, a hydroxyl or carboxyl group, —COR, —CN, an optionally branched alkyl radical containing from 1 to 6 carbon atoms which may optionally be substituted by halogen, —OH, —COOH, —COOR, —CN, —OR, —COR, or COR', a cycloalkyl radical containing from about 4 to 10 carbon atoms, an aryl or aralkyl radical containing from about 6 to 15 carbon atoms which may optionally be substituted by —OH, —R, —OR, —SR, halogen, —NO$_2$, —COR, —COOH, —CN, —COOR, —CONH$_2$, —OR', —SR' or —COR', or a C$_4$-C$_{10}$—heterocyclic radical containing oxygen and/or nitrogen as a hetero atom, wherein
- R represents an optionally halogen-substituted alkyl group containing from about 1 to 6 carbon atoms and
- R' represents an aryl group containing from about 6 to 12 carbon atoms.

3. The coating compositions of claim 2, wherein they contain from about 0.1 to 30% by weight, based on ammonium salts, of a sensitizer.

4. In a process for coating substrates with coating compositions based on polyurethane or epoxide resin precursors which harden in the presence of amines, the improvement wherein said compositions contain from about 0.1 to 40% by weight, based on solids content, of an ammonium salt of an α-ketocarboxylic acid corresponding to the following general formula:

A—CO—COOH  (I)

wherein
- A represents hydrogen, a hydroxyl or carboxyl group, —COR, —CN, —NO$_2$, an optionally branched alkyl radical containing from 1 to 6 carbon atoms which may optionally be substituted by halogen, —OH, —COOH, —COOR, —CN, —OR, —COR, or COR', a cycloalkyl radical containing from about 4 to 10 carbon atoms, an aryl or aralkyl radical containing from about 6 to 15 carbon atoms which may optionally be substituted by —OH, —R, —OR, —SR, halogen, —NO$_2$, —COR, —COOH, —CN, —COOR, —CONH$_2$, —OR', —SR' or —COR', or a C$_4$-C$_{10}$—heterocyclic radical containing oxygen and/or nitrogen as a hetero atom, wherein
- R represents an optionally halogen-substituted alkyl group containing from about 1 to 6 carbon atoms and
- R' represents an aryl group containing from about 6 to 12 carbon atoms, and said composition is irradiated with light having a wavelength of from about 250 to 500 nm.

5. In a process for coating substrates with coating compositions based on polyurethane or epoxide resin precursors which harden in the presence of amines, the improvement wherein said compositions contain from about 0.1 to 40% by weight, based on solids content, of an ammonium salt of an α-ketocarboxylic acid corresponding to the following general formula:

A—CO—COOH  (I)

wherein
- A represents hydrogen, a hydroxyl or carboxyl group, —COR, —CN, —NO$_2$, an optionally branched alkyl radical containing from 1 to 6 carbon atoms which may optionally be substituted by halogen, —OH, —COOH, —COOR, —CN, —OR, —COR, or COR', a cycloalkyl radical containing from about 4 to 10 carbon atoms, an aryl or aralkyl radical containing from about 6 to 15 carbon atoms which may optionally be substituted by —OH, —R, —OR, —SR, halogen, —NO$_2$, —COR, —COOH, —CN, —COOR, —CONH$_2$, —OR', —SR' or —COR', or a C$_4$-C$_{10}$—heterocyclic radical containing oxygen and/or nitrogen as a hetero atom, wherein
- R represents an optionally halogen-substituted alkyl group containing from about 1 to 6 carbon atoms and
- R' represents an aryl group containing from about 6 to 12 carbon atoms, and said composition is heated to between about 50°–130° C.

6. In a process for coating substrates with coating compositions based on polyurethane or epoxide resin precursors which harden in the presence of amines, the improvement wherein said compositions contain from about 0.1 to 40% by weight, based on solids content, of an ammonium salt of an α-ketocarboxylic acid corresponding to the following general formula:

A—CO—COOH  (I)

wherein

A represents hydrogen, a hydroxyl or carboxyl group, —COR, —CN, —NO$_2$, an optionally branched alkyl radical containing from 1 to 6 carbon atoms which may optionally be substituted by halogen, —OH, —COOH, —COOR, —CN, —OR, —COR, or —COR', a cycloalkyl radical containing from about 4 to 10 carbon atoms, an aryl or aralkyl radical containing from about 6 to 15 carbon atoms which may optionally be substituted by —OH, —R, —OR, —SR, halogen, —NO$_2$, —COR, —COOH, —CN, —COOR, —CONH$_2$, —OR', —SR' or —COR', or a C$_4$-C$_{10}$—heterocyclic radical containing oxygen and/or nitrogen as a hetero atom, wherein R represents an optionally halogen-substituted alkyl group containing from about 1 to 6 carbon atoms and R' represents an aryl group containing from about 6 to 12 carbon atoms, and said composition is irradiated with light having a wavelength of from about 250 to 500 nm and is heated to between about 50°–130° C.

7. The process of either claims 4, 5 or 6, wherein the coating compositions contain between about 0.1 to 30% by weight, based on the weight of the ammonium salts, of a sensitizer.

* * * * *